(12) United States Patent
Yang

(10) Patent No.: US 8,906,428 B2
(45) Date of Patent: Dec. 9, 2014

(54) MINERAL COMPOSITION, AND PREPARATION METHOD THEREOF

(76) Inventor: Dae Eun Yang, Anyang-si (KR)

( * ) Notice: Subject to any disclaimer, the term of this patent is extended or adjusted under 35 U.S.C. 154(b) by 16 days.

(21) Appl. No.: 13/988,759

(22) PCT Filed: Nov. 25, 2011

(86) PCT No.: PCT/KR2011/009052
§ 371 (c)(1),
(2), (4) Date: May 21, 2013

(87) PCT Pub. No.: WO2012/074245
PCT Pub. Date: Jun. 7, 2012

(65) Prior Publication Data
US 2013/0236558 A1     Sep. 12, 2013

(30) Foreign Application Priority Data

Nov. 29, 2010 (KR) .................. 10-2010-0119459
Apr. 19, 2011 (KR) .................. 10-2011-0036060

(51) Int. Cl.
| | | |
|---|---|---|
| A61K 36/00 | (2006.01) | |
| A61K 36/02 | (2006.01) | |
| A61K 35/12 | (2006.01) | |
| A23L 1/304 | (2006.01) | |
| A61Q 19/00 | (2006.01) | |
| A61K 8/96 | (2006.01) | |
| A61K 35/08 | (2006.01) | |

(52) U.S. Cl.
CPC ............. *A61K 35/08* (2013.01); *A61K 2800/10* (2013.01); *A23L 1/304* (2013.01); *A61Q 19/00* (2013.01); *A61K 8/965* (2013.01)

USPC ............. 424/725; 424/195.17; 424/522

(58) Field of Classification Search
None
See application file for complete search history.

(56) References Cited

U.S. PATENT DOCUMENTS

2004/0076687 A1    4/2004  Thompson

FOREIGN PATENT DOCUMENTS

| JP | 08-231382 | 9/1996 |
| JP | 2000-273033 | 10/2000 |
| KR | 10-2010-0009781 | 1/2010 |

OTHER PUBLICATIONS

International Search Report for PCT/KR2011/009052 mailed Jun. 21, 2012.

*Primary Examiner* — Qiuwen Mi
(74) *Attorney, Agent, or Firm* — Revolution IP, PLLC

(57) ABSTRACT

The mineral composition is prepared by mixing 100 parts by weight of deep sea water, dead sea water, underground salt water, sea water, aboveground salt water, mineral water, drinking water, fresh water, underground water or water with salt dissolved therein, 1-15 parts by weight of sea weed, 0.1-10 parts of weight of a vegetable oil, 0.1-10 parts by weight of an animal oil, 0.1-10 parts by weight of a soap or saponificated product of a vegetable oil, 0.1-10 parts by weight of a soap or saponificated product of an animal oil, 0.1-5 parts by weight of glycerin, 0.1-5 parts by weight of an alcohol, 0.1-5 parts by weight of baking powder, and 0.1-10 parts by weight of one or more acids of glacial acetic acid, phytic acid, malic acid, erythorbic acid, tartaric acid, citric acid, succinic acid and L-aspartic acid.

4 Claims, 4 Drawing Sheets

Fig. 1

Korea Testing & Research Institute

KTR

Korea Testing & Research Institute
(150-038) 88-2, Youngdungpo-dong 8Ga,
Youngdungpo-gu, Seoul, Korea
Tel: 02-2164-0011 Fax: 02-2634-0016

Test Report

Test Number: TAK-012213
Representative: Private
Name of Company: Yang, Chong-chul
Address: 46-12, Anyang 2-dong, Manan-gu, Anyang city Date of Receipt: August 27, 2009
Date of Test finished: September 8, 2009

Name of Sample: Mineral (Balan)

Result of Test

| Items of Test | Unit | Kinds of Samples | Resultant values | Test methods |
|---|---|---|---|---|
| Ca | % | 01 | 6.99 | EPA 3050 B : 1996(applied, ICP) |
| K | % | 01 | 0.01 | EPA 3050 B : 1996(applied, ICP) |
| Mg | % | 01 | 0.07 | EPA 3050 B : 1996(applied, ICP) |
| Li | % | 01 | non-detected | EPA 3050 B : 1996(applied, ICP) |
| Sr | % | 01 | 0.26 | EPA 3050 B : 1996(applied, ICP) |
| Mn | % | 01 | 0.02 | EPA 3050 B : 1996(applied, ICP) |
| Na | % | 01 | 0.39 | EPA 3050 B : 1996(applied, ICP) |
| F | mg/kg | 01 | non-detected | EN 14582 : 2002 |
| Cl | mg/kg | 01 | 121 | EN 14582 : 2002 |
| S | % | 01 | 0.09 | element analyzer (after dry) |

- Method Detection Limit -

F (50 mg/kg), Cl (50 mg/kg)
Use: For quality control
Remarks: 1. It is notified that this test report is a result of the tests conducted with the sample and sample name provided from the requester and does not guarantee the quality on the whole products.
2. This test report should not be used for the sakes of promotions, advertisement and law suits, and the use of this report is limited to the above use.

Researcher: Sun-il, Kim
Tel : 031-999-3125

Person charge in technology: Mu-sang, Ryu
E-mail : ymsang@ktr.or.kr

September 8, 2009
Chief of Korea Testing & Institute

Fig. 2

Korea Testing & Research Institute

Korea Testing & Research Institute
(150-036) 88-2, Youngdungpo-dong 8Ga,
Youngdungpo-gu, Seoul, Korea
Tel: 02-2164-0011 Fax: 02-2634-0016

Test Report

Test Number: TAK-012243
Representative: Private
Name of Company: Yang, Chong-chul
Address: 46-12, Anyang 2-dong,Manan-gu, Anyang city Date of Receipt: August 27, 2009
Date of Test finished: September 8, 2009

Name of Sample: Mineral (Balan)

Result of Test

| Items of Test | Unit | Kinds of Samples | Resultant values | Test methods |
|---|---|---|---|---|
| Fe | % | | 0.01 | EPA 3050 B : 1996(applied, ICP) |
| Cu | % | | 0.003 | EPA 3050 B : 1996(applied, ICP) |
| Zn | % | | 0.01 | EPA 3050 B : 1996(applied, ICP) |
| Se | mg/kg | | non-detected | EPA 3050 B : 1996(applied, ICP) |
| Cr | % | | 0.001 | EPA 3050 B : 1996(applied, ICP) |
| Mo | % | | non-detected | EPA 3050 B : 1996(applied, ICP) |
| $SiO_2$ | % | | 0.07 | KS L 5120 : 2004(applied) |
| I | mg/kg | | non-detected | EN 14582 : 2002 |
| moisture | % | | 81.1 | KS A 5301 : 1995(applied) |

-- Method Detection Limit --

I (50 mg/kg)
Use: For quality control
Remarks: 1. It is notified that this test report is a result of the tests conducted with the sample and sample name provided from the requester and does not guarantee the quality on the whole products.
2. This test report should not be used for the sakes of promotions, advertisement and law suits, and the use of this report is limited to the above use.

Sun-Il Kim
Researcher: Sun-il, Kim
Tel : 031-999-3125

Mu-Sang Lyu
Person charge in technology: Mu-sang, Ryu
E-mail : ymsang@ktr.or.kr

September 8, 2009
Chief of Korea Testing & Institute

Fig. 3

(153-803) 371-36, Gasan-dong,
Gumchon-gu, Seoul, Korea
Korea Analysis Research Institute  Tel: 02-339-4742-4
Fax: 02-389-4745

Test Report

Number of Issuance: 32 - 11 - 00052                     Number of Receipt: 32 - 11 - 00115
Name of Product: NTRAL Natural Combined Mineral Food    Date of manufacture (expiration date): -
Name of company: Mineral Korea                          Name of Requester: Yang, Jong-won
Address: Suchonri-24, Jangan-myeon, Hwasung city, Kyunggi-do, Korea
Date of Receipt: February 14, 2011                      Date of test finished: February 21, 2011
Type of food: -                                         Purpose of test: Test for references Test items and Results

| Test items | Criteria | Results | Items Judgments |
|---|---|---|---|
| calcium (mg/kg) | - | 161,339.96 | - |
| potassium (mg/kg) | - | 124.42 | - |
| magnesium (mg/kg) | - | 145.33 | - |
| iron (mg/kg) | - | 19.12 | - |
| phosphorus (mg/kg) | - | 1.52 | - |
| zinc (mg/kg) | - | 43.87 | - |
| manganese (mg/kg) | - | 4.02 | - |
| copper (mg/kg) | - | 0.40 | - |
| selenium (mg/kg) | - | 0.01 | - |
| molybdenum (mg/kg) | - | 0.02 | - |
| chrome (mg/kg) | - | 0.63 | - |
| nickel (mg/kg) | - | 1.86 | - |
| vanadium (mg/kg) | - | 4.8 | - |
| cobalt (mg/kg) | - | 8.8 | - |
| Sodium (mg/kg) | - | 606.56 | - |

Judgment :

| Tester | Kim, Dae-up |
|---|---|
| Person in charge | Rho, Ja-chun, Lee, Dong-hee |

(The above judgment covers only the requested test items)

Remarks :

It is notified that the test report is issued in compliance with the provisions of Article 4 (2) of
"Food and Sanitary Test Organ's Designation and Evaluation Standards"

February 21, 2011

Chief of Korea Analysis Research Institute 

* The above test report is a result of the samples offered from the requester and is prohibited
from using except for the above designated use.

MINERAL COMPOSITION, AND PREPARATION METHOD THEREOF

RELATED APPLICATIONS

This application is a 371 application of International Application No. PCT/KR2011/009052, filed Nov. 25, 2011, which in turn claims priority from Korean Patent Application Nos. 10-2011-036060, filed Apr. 19, 2011, and 10-2010-0119459, filed Nov. 29, 2010, each of which is incorporated herein by reference in its entirety.

TECHNICAL FIELD

The present invention relates to a mineral composition and in particular to a mineral composition and a preparation method thereof which can be used in cosmetics, food, medicine and to supplement minerals.

BACKGROUND ART

As a means for producing ocean deep sea water and maritime deep sea water or underground salt water, various ways are being adapted.

For example, ocean deep sea water and underground salt water are used in preparing mineral beverage or mineral cosmetics or in treating atopic dermatitis or for the sake of keratin removal and are used as a whitening agent. However, the effects of the above materials may decrease or the used aches in skins when they are used unless the salt components are eliminated, which causes inconveniences when in use.

DISCLOSURE OF INVENTION

Accordingly, the present invention is made based on the above mentioned conventional art and it is an object of the present invention to provide a mineral composition containing mineral components and a preparation method thereof which can be used in cosmetics, food, medicine and to supplement minerals.

To achieve the above objects, there is provided a mineral composition which is prepared in a manner that to 100 parts by weights of one or more selected from ocean deep sea water or deep sea water, dead sea water, maritime deep sea water, underground salt water, sea water, aboveground salt water, mineral water, drinking water, fresh water, underground water or salt-dissolved water is added 1-15 parts by weight of sea weed, 0.1-10 parts of weight of a vegetable oil, 0.1-10 parts by weight of an animal oil, 0.1-10 parts by weight of a soap or saponificated product of a vegetable oil, 0.1-10 parts by weight of a soap or saponificated product of an animal oil, 0.1-5 parts by weight of glycerin, 0.1-5 parts by weight of an alcohol, 0.1-5 parts by weight of baking powder, and 0.1-10 parts by weight of one or more acids of glacial acetic acid, phytic acid, malic acid, erythorbic acid, tartaric acid, citric acid, succinic acid and L-aspartic acid.

According to another aspect of the present invention, the mineral composition is used in cosmetic, food, medicine and supplement of minerals.

According to another aspect of the present invention, a preparation method of a mineral composition comprises preparing the mineral composition prepared in claim 1 in a cream type; and preparing the cream type mineral composition is a type of powder.

In addition, the step for preparing the mineral composition in a cream type comprises a step in which the mineral composition material is input in a stainless mixer tank and is mixed rotating for 30-40 minutes at a high speed, and the mineral coupled in the form of micro particles and the salt water are separated, and the salt water is eliminated, thus producing the coagulated cream type mineral composition; and the step for preparing the mineral composition in a powder type comprises a step in which 50 parts by weight of water is added to 100 parts by weight of the cream type mineral composition in a pot, and the mixture is heated at 100° C. for 30-40 minutes and then is rotated for 20-30 minutes in a centrifugal separator, so the mineral components are sunken, and the oil components float on the water, and the oil component-eliminated mineral components are washed 3-4 times with clean water, and the mineral components from which potassium components and glycerin, alcohol, baking powder and acid components are eliminated are hydrated and dried.

ADVANTAGEOUS EFFECTS

The mineral composition according to the present invention is prepared mixing ocean deep sea water, deep sea water, dead sea water, maritime deep sea water, underground salt water, sea water, aboveground salt water, mineral water, drinking water, fresh water, underground water, salt-dissolved water, seaweed, vegetable oil, animal oil, vegetable oil soap or saponificated product of the same, animal oil soap or saponificated product of the same, glycerin, alcohol, baking powder, glacial acetic acid, phytic acid, malic acid, erythorbic acid, tartaric acid, citric acid, succinic acid and L-aspartic acid.

By using the composition of the present invention in a human body, it has a great effect on the control of metabolism and a menstruation possibility control and is good at keratin, whitening and tough skins along with mineral supplement and metabolism-related diseases.

BRIEF DESCRIPTION OF DRAWINGS

FIGS. 1 to 4 are views illustrating the test reports conducted for the sake of a component analysis of a mineral composition according to the present invention.

BEST MODES FOR CARRYING OUT THE INVENTION

Figure 4:

The preferred embodiment of the present invention will be described with reference to the accompanying drawings.

The mineral composition of the present invention is prepared by mixing at least one of 1-15 parts by weight of sea weed, 0.1-10 parts of weight of a vegetable oil, 0.1-10 parts by weight of an animal oil, 0.1-10 parts by weight of a soap or saponificated product of a vegetable oil, 0.1-10 parts by weight of a soap or saponificated product of an animal oil, 0.1-5 parts by weight of glycerin, 0.1-5 parts by weight of an alcohol, 0.1-5 parts by weight of baking powder, and 0.1-10 parts by weight of one or more acids of glacial acetic acid, phytic acid, malic acid, erythorbic acid, tartaric acid, citric acid, succinic acid and L-aspartic acid.

The water is formed of one or more selected from ocean deep sea water, deep sea water, dead sea water, ocean deep sea water, maritime deep sea water, underground salt water, sea water, aboveground salt water, mineral water, drinking water and underground water, and the salt is formed on one or more selected from ocean deep water salt, deep sea salt, dead sea water salt, maritime deep sea water salt, underground salt water salt, sea water salt, aboveground salt water salt and aboveground salt, and the animal oil is formed of one or more selected from mammal oil, reptile oil, algae oil, fish oil and beeswax. The vegetable oil is formed of one or more selected from cacao butter, borage oil, green tea oil, peanut oil, soybean oil, hemp seed oil, sesame oil, cherry seed oil, pumpkin seed oil, camellia oil, apricot seed oil, evening primrose oil, unpolished rice oil, castor bean oil, avocado oil, almond oil, jojoba oil, grape seed oil, sunflower oil, olive oil, palm oil, coconut oil, hazelnut oil, canola oil, coconut palm oil, pine nut oil and walnut oil. The acid is formed of one or more selected from glacial acetic acid, phytic acid, malic acid, erythorbic acid, tartaric acid, citric acid, succinic acid and L-aspartic acid.

The thusly formed composition is input in a stainless mixer tank and is mixed for 30-40 minutes at a high speed, through which seaweed, animal oil, vegetable oil, animal oil soap, vegetable oil soap, glycerin, alcohol, baking is powder and acid components are mixed and divided in micro pieces, and then are coupled with the minerals contained in ocean deep sea water or deep sea water, dead sea water, fossil salt water, maritime deep sea water, peninsular deep sea water, shore underground rock salt water, inland underground rock salt water, sea water, aboveground salt water, drinking water, fresh water, underground water or river water, salt or seaweed and are separated from salt water. The mineral components coupled in the form of micro particles are lighter than the salt water, so they float on the salt water, and the salt water goes beneath the mineral components. 10 minutes later, the drainage valve is opened, and the salt water is drained out, thus producing a coagulated cream type mineral composition.

In order to separate the cream type mineral composition into an oil component and a mineral component, 50 parts by weight of water is added to 100 parts by weight of the cream type mineral composition, and the mixture is poured into a pot. The mixture is heated for 30-40 minutes at 100° C. and is rotated for 20-30 minutes in a centrifugal separator. The oil component and the mineral component are separated from each other, and the mineral component, which is heavier, sinks, and the oil component floats. The mineral component obtained after the oil component is eliminated is washed three or four times with clean water, and sodium component, glycerin, alcohol, salt, baking powder, acid components are eliminated, and the rests are dehydrated and dried, for thereby producing finally the powder type mineral compositions.

When the mineral compositions are extracted, the contents of the extracted mineral components can be increased when one or more selected from glacial acetic acid, phytic acid, malic acid, erythorbic acid, tartaric acid, citric acid, succinic acid and L-aspartic acid is used. As shown in FIGS. 1 and 2, there are shown the test reports when acid is not added, and FIGS. 3 and 4 show the test reports of the extracted amount of the mineral when acid is added. In case of calcium, FIG. 1 shows 69,900 mg/kg whereas FIG. 3 shows 161,340 mg/kg which is almost double (The unit 1% of FIG. 1 corresponds to 10,000 mg/kg). In case of potassium, the extracted amount is about 1.5 times, and in case of chlorine, as shown in FIGS. 1 and 4, it seems that the extracted amount increases significantly. In case of the test reports of FIGS. 3 and 4 which is performed in a state that acid is added, as compared to the test reports of FIGS. 1 and 2, the additionally extracted mineral components are selenium, molybdenum, fluorine, iodine, phosphorous, nickel, vanadium, cobalt, etc.

FIGS. 1 and 2 shows the test reports provided from Korea Test & Research Institute located at 88-2, Youngdungpo-dong 8Ga, Youngdungpo-gu, Seoul, Korea, and FIG. 3 is the test report provided from Korea Analysis Research Institute located at 371-36, Gasan-dong, Gumchon-gu, Seoul, Korea, and FIG. 4 is the test report provided from A & F located in 1183-5, Sa-dong, Sangrok-gu, Ahnsan city, Kyunggi-do, Korea. The above listed test institutes are all designated by Ministry of Food and Drug Safety of Korea. As shown therein, the mineral composition of the present invention contains many kinds of mineral components which are necessary for the sake of biological functions of a human body such as calcium, potassium, magnesium, iron, phosphorus, zinc, manganese, copper, selenium, molybdenum, chrome, nickel, vanadium, cobalt, chlorine, fluorine, sulfur, iodine, etc.

The invention claimed is:

1. A mineral composition which is prepared in a manner that to 100 parts by weights of one or more selected from ocean deep sea water or deep sea water, dead sea water, maritime deep sea water, underground salt water, sea water, aboveground salt water, mineral water, drinking water, fresh water, underground water or salt-dissolved water is added 1-15 parts by weight of sea weed, 0.1-10 parts of weight of a vegetable oil, 0.1-10 parts by weight of an animal oil, 0.1-10 parts by weight of a soap or saponificated product of a vegetable oil, 0.1-10 parts by weight of a soap or saponificated product of an animal oil, 0.1-5 parts by weight of glycerin, 0.1-5 parts by weight of an alcohol, 0.1-5 parts by weight of baking powder, and 0.1-10 parts by weight of one or more acids of glacial acetic acid, phytic acid, malic acid, erythorbic acid, tartaric acid, citric acid, succinic acid and L-aspartic acid.

2. The composition of claim 1, wherein the mineral composition is used in cosmetic, food, medicine and supplement of minerals.

3. A preparation method of a mineral composition, comprising:
    preparing the mineral composition in claim 1 in the form of a cream or a powder.

4. The method of claim 3, wherein the step for preparing the mineral composition in the form of a cream comprises putting the mineral composition materials in a stainless mixer tank; stirring for 30-40 minutes at a high speed to form microparticles, separating and eliminating water to obtain a coagulated cream; and wherein the step for preparing the mineral composition in the form of a powder comprises adding 50 parts by weight of water to 100 parts by weight of the cream in a pot, heating the mixture at 100° C. for 30-40 minutes, centrifuging for 20-30 minutes till the mineral components are precipitated, and the oil components are floating above the water, discarding the oil components, washing the mineral components 3-4 times with clean water, removing sodium components, glycerin, alcohol, baking powder and acid components, drying the remaining mineral components to form a powder.

* * * * *